United States Patent [19]

Jurd

[11] 4,391,828
[45] Jul. 5, 1983

[54] DIBUTYLORTHOBENZYLMETHOXYBEN-ZENES AND DIBUTYLORTHOCINNAMYLMETHOXY-BENZENES AS MOSQUITO LARVAE GROWTH INHIBITORS

[75] Inventor: Leonard Jurd, Berkeley, Calif.

[73] Assignee: The United States of America as represented by the Secretary of Agriculture, Washington, D.C.

[21] Appl. No.: 370,019

[22] Filed: Apr. 20, 1982

[51] Int. Cl.³ .................. A01N 31/14; C07C 43/205
[52] U.S. Cl. .................................. 424/340; 424/341; 568/640; 568/641; 568/631
[58] Field of Search .................. 568/640, 641, 631; 424/340, 341

[56] References Cited

U.S. PATENT DOCUMENTS 3,839,586 10/1974 Ludvik ............................. 424/346
3,920,846 11/1975 Hanauye et al. .................. 424/346
3,973,040  8/1976 Jurd ................................. 424/346
4,357,344 11/1982 Jurd ............................. 568/640 X

FOREIGN PATENT DOCUMENTS 2425713 1/1975 Fed. Rep. of Germany .

OTHER PUBLICATIONS

*Mosquito News*, vol. 31, No. 4, pp. 513-516, (1971).
*Chemical Abstracts*, vol. 80, No. 768h, (1974).

*Primary Examiner*—Bernard Helfin
*Attorney, Agent, or Firm*—M. Howard Silverstein; David G. McConnell; Margaret A. Connor

[57] ABSTRACT

Novel dibutylorthobenzylmethoxybenzenes having the structure

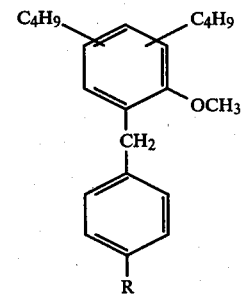

wherein R is hydrogen, lower alkyl or lower alkoxy and novel dibutylorthocinnamylmethoxybenzenes are disclosed as growth inhibitors for mosquito larvae.

9 Claims, No Drawings

DIBUTYLORTHOBENZYLMETHOXYBENZENES AND DIBUTYLORTHOCINNAMYLMETHOXYBENZENES AS MOSQUITO LARVAE GROWTH INHIBITORS

BACKGROUND OF THE INVENTION

1. Field of Invention

This invention relates to and has among its objects the the provision of novel organic compounds and the use thereof in insect control, particularly inhibition of the growth of mosquito larvae. Further objects of the invention will be evident from the following description wherein parts and percentages are by weight unless otherwise specified. The symbol $\phi$ is used herein to represent the phenyl

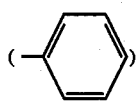

group.

2. Description of the Prior Art

One means for biological control of insect populations involves the use of compounds which inhibit the growth of insect larvae. Such compounds are referred to in the art as insect growth regulators or juvenile hormone mimics. Juvenile hormones are essential for growth and development of young larvae. The last instar larvae are equipped with internal physiological mechanisms which interrupt the secretion of these juvenile hormones resulting in a replacement of larval growth by pupal and adult growth—a process generally known as metamorphosis. Provision of an exogenous supply of a juvenile hormone or hormone analog at a critical period in larval development causes partial or complete inhibition of metamosphosis. Juvenile hormone mimics do not kill the larvae, but rather prevent the growth thereof beyond the larval or pupal stage. Consequently, the number of adults is substantially reduced. The juvenile hormone mimics actually cause several different situations, all of which result in controlling insect population. First of all, most of the treated larvae do not reach adulthood. Thus, the larvae survive for a period of time (possibly an entire growing season) as either larvae or pupae, and then die. During that period the larvae are, of course, very susceptible to predation and injurious climatic conditions. Furthermore, they are themselves incapable of reproduction, thus reducing the insect population for the next growing season. Secondly, some of the treated larvae may develop to various stages of adulthood. For example, the adult insect my only partially eclose, i.e., emerge from the larval or pupal shell. On the other hand, full eclosion may occur but the adult insect is either malformed or dead. In either case, the population of adult insects is substantially reduced.

The growth-inhibiting compounds have many advantages over insecticides and the like. First, the growth-inhibitors do not yield unwanted ecological side effects. Secondly, since the growth inhibitors act as juvenile hormone mimics, the insects do not develop a tolerance to the compounds. Thus, the compounds will not eventually become ineffective. Third, the growth-inhibiting compounds are not harmful to beneficial insects or mammals because they are quite specific for a particular kind of insect.

Polybutylorthobenzyl and parabenzyl phenols have been disclosed as larvae growth-inhibiting compounds. *Mosquito News,* Volume 31, No. 4, pp 513–516 (1971) and *Chemical Abstracts,* Volume 80, No. 768 h (1974) disclose compounds to control mosquitos having the structure

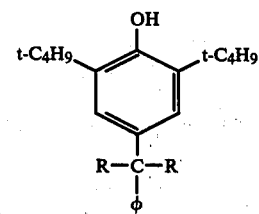

wherein R is independently hydrogen or methyl.

Hanauye et al (U.S. Pat. No. 3,920,846) and Hanaue (German Offen. 2,425,713) disclose compounds having juvenile hormone activity effective in combatting mosquito larvae having the general formula

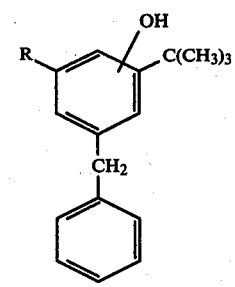

wherein R is hydrogen or t-butyl, with the proviso that the hydroxyl group is in the ortho position with respect to R and at least one t-butyl group is present in the ortho position with respect to the hydroxyl group.

Ludvik (U.S. Pat. No. 3,839,586) teaches the method of preventing mosquito larvae from developing into adult stage by exposing the larvae to compounds of the structure

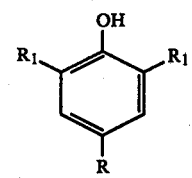

wherein R is hydrogen, isopropylphenyl, alkyl of from 1 to 6 carbons, alkoxy of from 1 to 6 carbons and thioalkyl of from 1 to 6 carbons and $R_1$ is t-butyl, t-pentyl, or cyclohexyl.

Jurd (U.S. Pat. No. 3,973,040) discloses poly-t-butyl-2-cinnamylphenols as mosquito larvae growth inhibitors of the structure

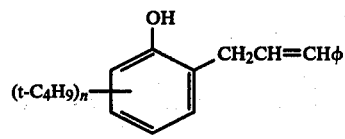

wherein n is 2 or 3.

SUMMARY OF THE INVENTION

I have found that certain ditertiarybutylorthobenzylmethoxybenzenes and ditertiarybutylorthocinnamylmethoxybenzenes control mosquito populations by inhibiting the growth of mosquito larvae. Surprisingly, the instant compounds are many times more effective than known growth inhibitors which are close in chemical structure. For example, the orthobenzylphenols and orthocinnamylphenols which serve as intermediates to the compounds of the invention are significantly less effective as growth inhibitors. This structure/activity effect has not been previously recognized. Furthermore, the instant compounds appear to lack the mutagenic properties possessed by many known larval growth inhibitors.

The novel compounds of the invention may be categorized as follows:

Group I. Dibutylorthobenzylmethoxybenzenes of the structure

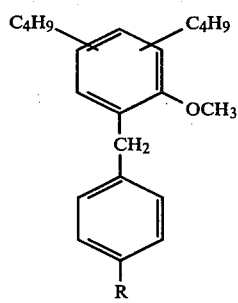

wherein R is hydrogen, lower alkyl containing from 1 to 6 carbon atoms or lower alkoxy containing from 1 to 6 carbon atoms; and Group II. Dibutylorthocinnamylmethoxybenzenes of the structure

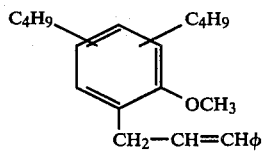

The compounds of the invention are administered to mosquito larve in an amount sufficient to inhibit larval growth.

The primary advantage of the novel growth inhibitors of the invention is that they are many times more effective than known polybutylbenzylphenol growth inhibitors having closely related chemical structures. This increased growth activity of the compounds of the invention is unexpected and not shared by other closely related compounds. For example compounds having ethoxy or higher groups in place of the methoxy group are many times less effective in my method. Similarly, methoxybenzene compounds having substitution on the methylene group of the benzylic carbon atom do not have the effective growth inhibiting activity of the compounds of the invention.

Other advantages of the compounds are that they are effective against mosquitos resistant to organophosphate insecticides.

DESCRIPTION OF THE PREFERRED EMBODIMENTS

The highly effective novel growth inhibitors of the invention are applied in a growth-inhibiting amount to the habitat or breeding place of the mosquito larvae, e.g. added to the water wherein larvae are present. As a result, the growth of the mosquito larvae beyond the larval or pupal stage is inhibited so that few, if any, adult mosquitos are formed. The concentration of the compound required to achieve growth inhibition varies depending on the activity of the selected compound. In any particular case the appropriate amount can be readily determined by pilot tests well-known to entomologists. In many cases good results have been attained where the compounds are applied in a concentration of about 0.001 to 1 ppm (parts per million) in bodies of water where the mosquito larvae exists. Because the compounds of the invention are effective in very minor concentrations, it is preferred that they be dissolved or suspended in a carrier prior to application to the breeding centers. The solution or suspension increases the bulk, and thus makes it easy to administer small amounts of the compounds to the mosquito breeding area. Solvents appropriate for this purpose should be volatile ones, such as acetone, ethyl ether, ethanol, benzene, xylene, petroleum naphtha, and the like.

It is within the compass of the invention to use a single compound as herein described or mixtures of two or more of these compounds.

The compounds of the invention are effective mosquito growth inhibitors against more than one species and genus of mosquito larvae. They have been found particularly effective against, but not limited to Aedes such as *Aedes aegypti*, (yellow fever mosquito) and *Aedes taeniorhyrnchos*; Anopheles such as *Anopheles quadrimaculatus* (malaria mosquito) and *Anopheles albimanus*. They may also be used against the genera Culex such as the house mosquito, *Culex pipiens*, as well as those of the genera Culiseta, Deinocerites, Haemagogus, Mansonia, Megarhinus, Orthopodomyia, Psorophora, Sabethes, Toxorhynchites, Uranotaenia and Wyeomia.

Typical examples of compounds which may be used in the method of the invention are the following:

Group I: 2,4-bis (1,1-dimethylethyl)-6-(phenylmethyl)-methoxybenzene; 2,4-bis(1,1-dimethylethyl)-6-[(4-alkylphenyl)methyl]-methoxybenzene wherein the 4-alkyl group is methyl, ethyl, propyl, butyl, pentyl, and hexyl respectively; and 2,4-bis(1,1-dimethylethyl)-6-[(4-alkoxylphenyl)methyl]methoxybenzene wherein the 4-alkoxyl group is methoxy, ethoxy, propoxy, butoxy, pentoxy, and hexoxy, respectively.

Group II: 2,4-bis (1,1-dimethylethyl)-6-(3-phenyl-2-propenyl)-methoxybenzene.

It is a critical feature of the invention that the alkoxy group on the dibutylphenyl moity be methoxy and that it be ortho to the phenylmethyl (benzyl) group. It is also a critical feature that there is an unsubstituted methylene group on the benzylic carbon.

The novel methoxybenzenes may be prepared by refluxing the appropriate polybutylphenol with a methylator such as dimethylsulfate or methyl iodide.

The synthesis of Group I compounds is illustrated by the following formulas

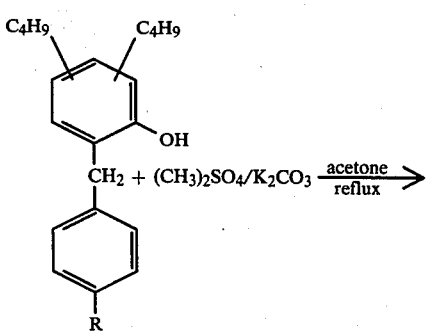

wherein R is defined as described above.

Group II compounds are synthesized as follows:

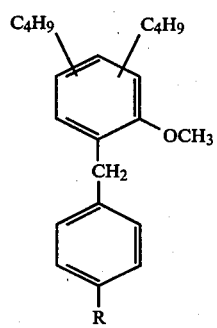

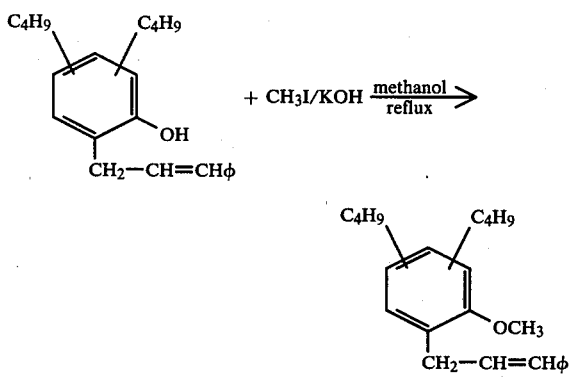

EXAMPLES

The invention is further demonstrated by the following illustrative examples. Temperatures are in degrees Centigrade.

EXAMPLE 1

Synthesis of Group I Compounds

A. 2,4-Bis(1,1-dimethylethyl)-6-(phenylmethyl)methoxybenzene:

A mixture of 2,4-bis(1,1-dimethylethyl)-6-(phenylmethyl)phenol (10 g), methyl iodide (10 g), potassium carbonate (10 g) and acetone (40 ml) was boiled under reflux for 16 hours, concentrated and diluted with water. The oily product was extracted with ether and distilled. The fraction, b.pt. 170°–175° at 0.5 mm Hg crystallized from methanol to give colorless needles, m.p. 68° (7.5 g). (Found: C,85.0;H,9.62; calc. for $C_{22}H_{30}O$: C,85.1;H,9.74%. The molecular weight (mass) of the product as determined by mass spectrometry was 310.2296; calc. 310.2297). The proton magnetic resonance ($^1$Hnmr) spectrum at 100 MHz in deuterated chloroform (CDCl$_3$) exhibited absorbance as follows: $\delta$1.20, 9 protons (H), singlet (S); $\delta$1.38, 9H,S; $\delta$3.66,3H,S; $\delta$4.03, 2H,S; $\delta$6.90,1H, doublet (D) (J=2 Hz); $\delta$7.18,6H,S.

B. 2,4-Bis (1,1-dimethylethyl)-6-[(4-methoxyphenyl)methyl]-methoxybenzene:

A mixture of 2,4-bis(1,1-dimethylethyl)-6-[(4-methoxyphenyl)methyl]phenol (32 g), dimethyl sulfate (25 g), anhydrous potassium carbonate (40 g) and acetone (100 ml) was boiled under reflux for eight hours, concentrated and diluted with excess of water. The solid product was collected and recrystallised from acetone-methanol to give colorless needles, m.p. 98°–99° (28 g.). (Found: C,81.0;H,9.41; calc. $C_{23}H_{32}O_2$: C,81.1;H,9.47%). The $^1$Hmmr spectrum (CDCl$_3$) exhibited the following: $\delta$1.21,9H,S; $\delta$1.38,9H,S; $\delta$3.66,3H,S; $\delta$3.73,3H,S; $\delta$3.98,2H,S; $\delta$6.78,2H,D(J=8 Hz); $\delta$6.90,1H,D(J=2 Hz), $\delta$7.06,2H,D(J=8 Hz), $\delta$7.20,1H,D (J=2 Hz).

EXAMPLE 2

Synthesis of Group II Compounds

C. 2,4-Bis(1,1-dimethylethyl)-6-(3-phenyl-2-propenyl)-methoxybenzene:

A mixture of 2,4-bis(1,1-dimethylethyl)-6-(3-phenyl-2-propenyl)phenol (14 g ), methyl iodide (10 ml), potassium hydroxide (15 g) and methanol (25 ml) was boiled under reflux for two hours, concentrated and diluted with water. The solid product was collected and recrystalized from acetone-methanol to give long colorless needles, m.p. 68°–69° (13.0 g). (Found: C,87.5;H,9.52; calc. for $C_{24}H_{32}O$: C,85.7;H,9.60%). $^1$Hnmr spectrum (CDCl$_3$): $\delta$1.25,9H,S; $\delta$1.38,9H,S; $\delta$3.56,2H,D(J=5 Hz), $\delta$3.72,3H,S; $\delta$6.41,2H, multiplet (M); $\delta$7.05–7.43,7H,M.

EXAMPLE 3

Growth-Inhibition Tests

Twenty-five late third-and early fourth-stage mosquito larve were placed in a 500-ml glass jar (9X8.5 cm diam) containing 100 ml of well water, 0.05g ground hog supplement for larval food, and a known amount of the test compound in not more than 1.0ml acetone. The jars were covered with cloth netting and held in constant temperature incubators at 26.7°–28.9° C. and 65–75% relative humidity; a low level of illumination (ca. 0.5 foot candles inside the incubators) was maintained during nonworking hours. After seven days, the jars were examined for the number of dead pupae, the number of adults that were dead or unable to complete eclosion and the number of exuvia. The live adults were observed for gross abnormalities. Tests were replicated for at least one concentration and a control was set with each test series. Several concentrations of each compound were tested so that a dose-response relationship could be established.

The effectiveness of the compound in inhibiting growth was determined by adding the numbers of dead larvae and pupae and the numbers of adults that were dead, unable to complete eclosion, and malformed. This sum was corrected by Abbott's formula (to adjust for the number of larvae or pupae which would die naturally). The results are expressed as LC 50 or LC 90, i.e., the concentration of growth inhibitor in ppm that would prevent and/or retard the growth in 50% or 90%, respectively, of the treated larvae.

As shown in Table I, the compounds of the invention are active against several genera and species of mosquitos. Tables II–IV show that the methoxybenzene compounds are many times more effective as growth inhibitors than the phenols from which they are derived, than compounds having ethoxy or higher groups in place on the methoxy group and methoxybenzenes having substitution on the methylene group of the benzylic carbon. The sumbol (†) represents the tertiarybutyl (dimethylethyl) group.

TABLE I

| TEST COMPOUND | ANOPHELES QUADRIMACULATUS | | ANOPHELES ALBIMANUS | | AEDES AEGYPTI | | AEDES TAENIORHYNCHOS | |
|---|---|---|---|---|---|---|---|---|
| | LC-50 | LC-90 | LC-50 | LC-90 | LC-50 | LC-90 | LC-50 | LC-90 |
| A | 0.065 | 0.092 | 0.014 | 0.025 | | | 0.026 | 0.164 |
| B | | 0.032 | .005 | 0.009 | 0.005 | 0.099 | 0.009 | 0.023 |

TABLE II

| TEST COMPOUND | STRUCTURE | ANOPHELES QUADRIMACULATUS | |
|---|---|---|---|
| | | LC-50 | LC-90 |
| A | †—⟨benzene-OCH$_3$⟩—CH$_2$—⟨phenyl⟩ | 0.065 | 0.092 |
| A-I[1] | †—⟨benzene-OH⟩—CH$_2$—⟨phenyl⟩ | 0.20 | 1.37 |
| A-II[1] | †—⟨benzene-OCH$_2$CH$_3$⟩—CH(CH$_3$)—⟨phenyl⟩ | >1.0 | |
| A-III[1] | †—⟨benzene-OCH$_3$⟩—CH(CH$_3$)—⟨phenyl⟩ | >1.0 | |

[1] Not in accordance with the invention

TABLE III

| TEST COMPOUND | STRUCTURE | ANOPHELES QUADRIMACULATUS | |
|---|---|---|---|
| | | LC-50 | LC-90 |
| B | †—⟨benzene-OCH$_3$⟩—CH$_2$—⟨phenyl⟩—OCH$_3$ | | 0.032 |
| B-I[1] | †—⟨benzene-OH⟩—CH$_2$—⟨phenyl⟩—OCH$_3$ | 0.120 | 0.225 |
| B-II[1] | †—⟨benzene-OCH$_2$CH$_3$⟩—CH$_2$—⟨phenyl⟩—OCH$_3$ | 0.074 | 0.285 |
| B-III[1] | †—⟨benzene-CH$_2$CH=CH$_2$⟩—CH$_2$—⟨phenyl⟩—OCH$_3$ | | >1.0 |
| B-IV[1] | †—⟨benzene-OCH$_3$⟩—CH(CH$_3$)—⟨phenyl⟩—OCH$_3$ | 0.242 | 0.556 |
| B-V[1] | †—⟨benzene-OCH$_2$CH$_3$⟩—CH(CH$_3$)—⟨phenyl⟩—OCH$_3$ | | >1.0 |

TABLE IV

| TEST COMPOUND | STRUCTURE | ANOPHELES QUADRIMACULATUS | |
|---|---|---|---|
| | | LC-50 | LC-90 |
| C | †—⟨benzene-OCH$_3$⟩—CH$_2$—CH=CHφ | 0.026 | 0.089 |
| C-I[1] | †—⟨benzene-OH⟩—CH$_2$CH=CHφ | 0.152 | 0.399 |
| C-II[1] | †—⟨benzene-OCH$_2$CH$_3$⟩—CH$_2$—CH=CHφ | 0.189 | 1.042 |

[1] Not in accordance with the invention.

EXAMPLE 4

Mutagenicity Studies

The mutagenic activity of Compound B was tested by the standard Ames' Salmonella/microsome procedure, which is reported to show approximately 90% correlation with development of mammalian cancers (Ames et al., *Mutation Research*, Vol. 31, p. 347,1975; McCann et al., *Proceedings of the National Academy of Science*, Vol. 72, p. 5135, 1975). Tester strains TA-100,TA-98,TA-1537 and the plate test method were used, employing concentrations of 10,100, and 1000 ug of compound per plate. The metabolic activation mixture (S-9 mix) used the 9000 times g supernatant of Aroclor 1254-induced rat liver homogenate at a level of 100 ul per ml of S-9 mix. The results indicate that in the strains tested Compound B is non mutagenic, either without or with metabolic activation.

Preparation of the Intermediates

Novel Synthesis of starting phenol

The phenol precursors of the compounds of the invention may be prepared by the following novel synthesis:

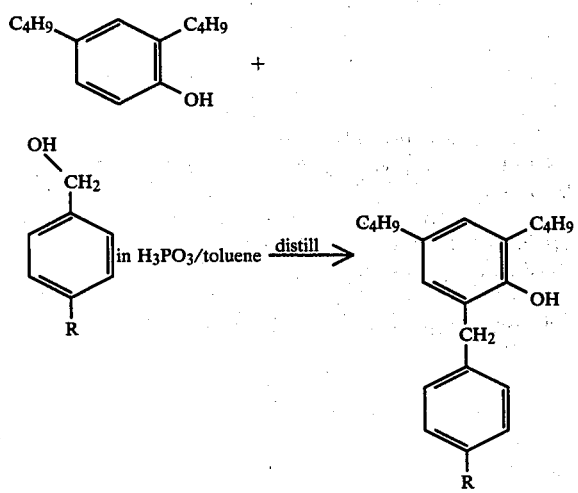

wherein R is defined as above.

EXAMPLE A

Novel synthesis of 2,4-bis(1,1-dimethylethyl)-6-[(4-methoxyphenyl)methyl]phenol (Compound B-I).

A mixture of 2,4-di-t-butylphenol (41.2 g), phosphorous acid (2 drops) and toluene (5 ml) was heated to 180°–200° in a three-necked flask fitted with a Dean-Stark trap containing toluene. 4-Methoxybenzyl alcohol (27.6 g) was melted and added in a slow stream to the mixture during 45 min. Heating was continued for a further 15 min by which time the theoretical amount of water (3.6 ml) had distilled. The reaction mixture was then distilled under pressure to give a pale yellow oil which rapidly crystallized. Recrystalization from methanol yielded colorless needless, m.p. and mixed m.p. with authentic material, 84°–85°; yield 59.3 g (91%). Found: C,80.9;H,9.26; calc for $C_{22}H_{30}O_2$:C,81.0;H,9.21); $^1$Hmmr spectrum: δ1.30,9H,S; δ1.38,9H,S; δ3.79,3H,S; δ3.83,2H,S; δ4.61,H,S; δ6.84,2H,D(J=8 Hz); δ7.03, 1H,D(J=2 Hz); δ7.14,2H,D(J=8 Hz); δ7.23,1H,D(J=2 Hz).

Alternatively, the intermediate phenols may be prepared as follows:

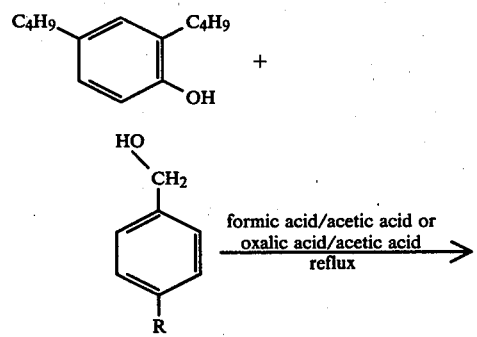

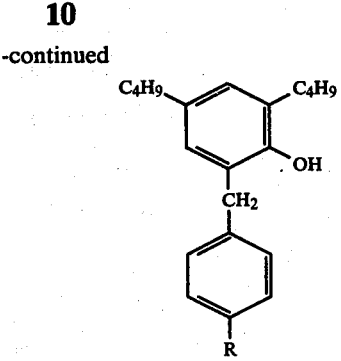

wherein R is defined as above.

EXAMPLE B

Synthesis of Compound B-I.

A solution of 2,4-ditertiarybutylphenol (57.5 g), 4-methoxybenzyl alcohol (34.5 g), and oxalic acid (2 g) in acetic acid (80 ml) and water (2 ml) was refluxed for seven hours, diluted with water and extracted with chloroform. Distillation of the chloroform extract gave an oil, b.p. 200–210 at 2 mm Hg, which crystallized (58 g,71.4%). Recrystallization from methanol yielded colorless needles, m.p. 84–85; $^1$Hmmr spectrum: δ1.30,9H,S; δ1.38,9H,S; δ3.79,H.S; δ3.83,2H,S; δ4.62,1H,S; δ6.84,2H, D(J=8 Hz); δ7.03,1H,D(J=2 Hz); δ7.14,2H,D(J=8 Hz); δ7.23,1H,D(J=2 Hz).

Having thus described my invention, I claim:

1. A compound of the structure

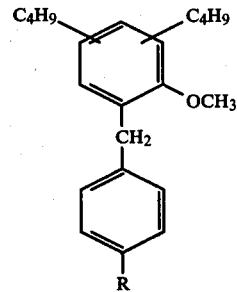

wherein R is hydrogen, lower alkyl containing from 1 to 6 carbon atoms or lower alkoxy containing from 1 to 6 carbon atoms.

2. The compound of claim 1 which is 2,4-bis(1,1-dimethylethyl)-6-(phenylmethyl)methoxybenzene.

3. The compound of claim 1 which is 2,4-bis(1,1-dimethylethyl)-6-[(4-methoxyphenyl)methyl]methoxybenzene.

4. A compound of the structure

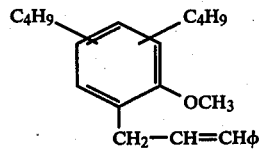

5. The compound of claim 4 which is 2,4-bis(1,1-dimethylethyl)-6-(3-phenyl-2-propenyl)methoxybenzene.

6. A method of inhibiting growth of mosquito larvae, which comprises:

administering to the larvae an effective growth inhibiting amount of a compound selected from the group consisting of (a) compounds of the structure

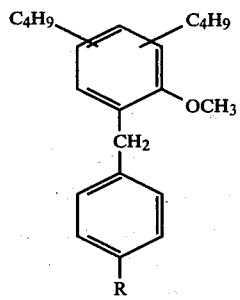

wherein R is hydrogen, lower alkyl containing from 1 to 6 carbon atoms or lower alkoxy containing from 1 to 6 carbon atoms, and (b) compounds of the structure

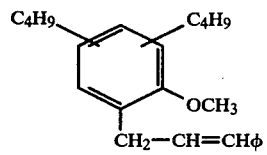

7. The method of claim 6 wherein said compound is 2,4-bis(1,1-dimethylethyl)-6-(phenylmethyl)methoxybenzene.

8. The method of claim 6 wherein said compound is 2,4-bis(1,1-dimethylethyl)-6-[(4-methoxyphenyl)methyl]methoxybenzene.

9. The method of claim 6 wherein said compound is 2,4-bis-(1,1-dimethylethyl)-6-(3-phenyl-2-propenyl)methoxybenzene.

* * * * *

UNITED STATES PATENT AND TRADEMARK OFFICE
CERTIFICATE OF CORRECTION

PATENT NO. : 4,391,828
DATED : July 5, 1983
INVENTOR(S) : Leonard Jurd

It is certified that error appears in the above-identified patent and that said Letters Patent is hereby corrected as shown below:

Column 8, line 30, add --[1]Not in accordance with the invention. --.

Signed and Sealed this

Twenty-fourth Day of January 1984

[SEAL]

Attest:

GERALD J. MOSSINGHOFF

*Attesting Officer*     *Commissioner of Patents and Trademarks*